United States Patent
Soejima

(10) Patent No.: US 8,170,176 B2
(45) Date of Patent: May 1, 2012

(54) X-RAY CT SYSTEM, A RECORDING MEDIUM THAT STORES CONTROL PROGRAM FOR THE SAME AND A METHOD OF DETERMINING AN IMAGE RESULT IN CASE OF CAPTURING CT IMAGES

(75) Inventor: Nobukatsu Soejima, Otawara (JP)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 206 days.

(21) Appl. No.: 12/700,996

(22) Filed: Feb. 5, 2010

(65) Prior Publication Data
US 2010/0208864 A1      Aug. 19, 2010

(30) Foreign Application Priority Data

Feb. 17, 2009   (JP) .................................. 2009-033392
Jan. 14, 2010   (JP) .................................. 2010-005936

(51) Int. Cl.
    *H05G 1/32* (2006.01)
(52) U.S. Cl. ............................................. 378/20; 378/4
(58) Field of Classification Search ................ 378/4, 16, 378/19–20
    See application file for complete search history.

(56) References Cited

U.S. PATENT DOCUMENTS
2007/0140409 A1*   6/2007   Arenson et al. .................... 378/4

FOREIGN PATENT DOCUMENTS
JP           2007-267783 A      10/2007

* cited by examiner

*Primary Examiner* — Hoon Song
(74) *Attorney, Agent, or Firm* — Knoble Yoshida & Dunleavy, LLC

(57) ABSTRACT

An imaging-condition setting part that sets a plurality of CT-image imaging conditions, including an electric amount for driving and controlling an X-ray tube during CT imaging, based on a scout image that has been imaged by irradiating X-rays from the X-ray tube, to a subject on a top board, that has been stopped at least one of said first position and said second position; and a calculating part that judges whether there are any detection elements that are expected to detect an X-ray dosage exceeding a predetermined value and outputs the judgment result when the X-ray tube is stopped at least one of the first position and the second position relative to the subject on the top board and X-rays are irradiated from the X-ray tube through driving and controlling based on the electric amount.

7 Claims, 7 Drawing Sheets

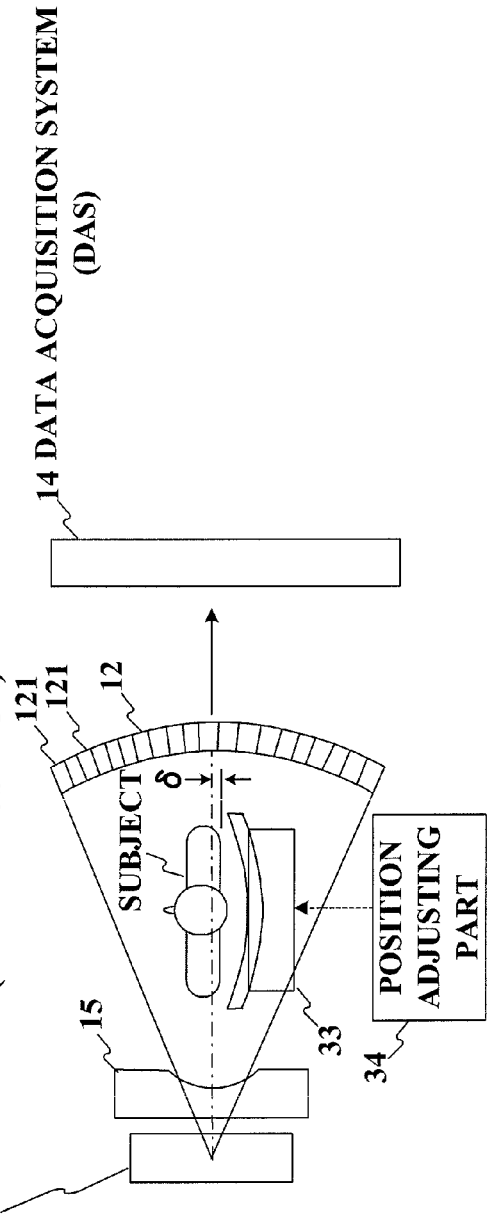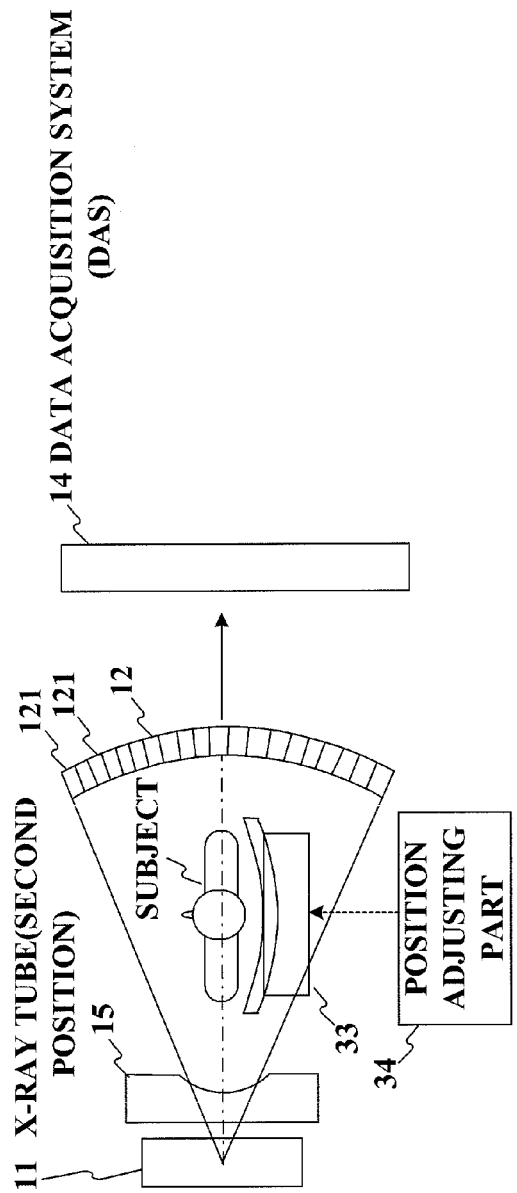
FIG.5A
FIG.5B

X-RAY CT SYSTEM, A RECORDING MEDIUM THAT STORES CONTROL PROGRAM FOR THE SAME AND A METHOD OF DETERMINING AN IMAGE RESULT IN CASE OF CAPTURING CT IMAGES

BACKGROUND OF THE INVENTION

1. Field of the Invention

The present invention relates to an X-ray CT system, a recording medium that stores a control program for the same, and a method of determining an imaging result in case of capturing CT images.

The present invention particularly relates to an X-ray CT system and A recording medium that stores a control program for the same that set CT-image imaging conditions based on a scout image of a subject.

Herein, examples of the CT-image imaging conditions include tube voltage, tube current, X-ray dosage, field of view (FOV), collimator aperture, slice thickness, wedge filter type, operation of the wedge filter, and position of the top board.

2. Description of the Related Art

In a conventional X-ray CT system, an engineer (operator) selects CT-image imaging conditions recommended by the system based on an obtained scout image. Additionally, the engineer visually confirms the size of the subject and sets the CT-image imaging conditions based on past experience, etc.

Additionally, a conventional X-ray CT system images a scout image of the subject and confirms the size of the subject based on the X-ray dosage introduced to detection elements during imaging of the scout image to set the CT-image imaging conditions and then images CT images under those CT-image imaging conditions. Alternatively, the scout images are each imaged by rotating and stopping the X-ray tube at each position located above the subject (in the direction of 0°) and located to the side of the subject (in the direction of 90°) and irradiating X-rays to the subject from these two directions. The engineer confirms the size of the subject based on each scout image imaged from the two directions to set the CT-image imaging conditions and then images CT images under those CT-image imaging conditions.

As described above, in a conventional X-ray CT system, CT-image imaging conditions are set based on either visual confirmation by the engineer or the scout image and CT images are then imaged under those CT-image imaging conditions.

Next, the following technologies have been adopted in X-ray CT systems. A technology has been adopted in which the engineer sets the tube current high when imaging bony regions such as the shoulder and pelvis in order to increase the X-ray dosage and sets the tube current low when imaging regions such as the chest (lungs) in order to decrease the X-ray dosage.

Recent X-ray CT systems adopt a technology that changes the conditions of the tube current depending on the region to be imaged or a technology that differentiates the X-ray dosage of the X-ray tube from the direction of 0° and 180° from the X-ray dosage of the X-ray tube from the direction of 90° and 270°. The engineer selects the above technologies according to the application.

Additionally, a plurality of detection elements is arranged in the direction of the fan angle of the X-ray tube. A wedge filter is provided between the X-ray tube and the subject in order to adjust the X-ray dosage of the X-rays that are introduced to each detection element by passing through or without passing through the subject. Therefore, for the central detection elements located on the centerline that bisects the fan angle, by assuming that X-rays that have been transmitted through the thick central part of the subject will be introduced, a large amount of X-rays is irradiated from the X-ray tube, whereas for the detection elements between the center and the ends, assuming that X-rays that have been transmitted through a thin part of the subject or that have not been transmitted through the subject will be introduced, a small amount of X-rays is irradiated from the X-ray tube according to the thickness of the subject that is penetrated.

When the X-rays are irradiated to the subject, the center of which has been located at the centerline that bisects the fan angle, according to the X-ray dosages described above, a large amount of X-rays is transmitted to the center of the subject and thereby sufficiently attenuated in the subject, and the X-ray dosage introduced to the center of the detection elements is therefore decreased. The introduction of data falls within the assumed count. A small amount of X-rays is either slightly transmitted through the subject or is introduced directly to the end of the detection elements without being transmitted through the subject.

Additionally, there is a technology that forms a preferred irradiation range for the diagnosis-target section by arranging a plurality of wedge filters with curves, the curvatures of which are each different, and moving the wedge filters in the body-axis direction of the subject (e.g., Japanese Unexamined Patent Application Publication No. 2007-267783).

However, in the abovementioned conventional X-ray CT system, in cases of setting CT-image imaging conditions in which the X-ray dosage is large relative to the size of the subject, the X-ray dosage introduced to the detection elements is excessively increased, causing an overflow of the detection elements and thereby generating artifacts (abnormal images). Unnecessary and excessive exposure to X-rays also leads to problems.

When the center of the subject is located by shifting the center from the centerline that bisects the fan angle, a large amount of X-rays is either slightly transmitted through the subject or is introduced directly to the detection elements in the center without being transmitted through the subject. The X-rays that are slightly transmitted and introduced to the detection elements in the center are indicated with a broken line in FIG. 7. The X-rays indicated with a dashed line undergo little attenuation in the subject and therefore, an X-ray dosage that is higher than expected is introduced to the detection elements in the center, leading to a problem that an overflow of the detection elements may be generated. When X-rays are introduced at a dosage that is higher than expected, ring artifacts (abnormal images) may be generated.

SUMMARY OF THE INVENTION

This invention is intended to provide an X-ray CT system, a recording medium that stores a control program for an X-ray CT system and a method of determining an imaging result in case of capturing CT images, which allows judgment information to be obtained for avoiding generation of an overflow by detection elements.

A first aspect of the invention is an X-ray CT system comprising: a mount; an X-ray tube configured to irradiate a beam with a fan angle; a top board on which a subject is placed; an X-ray detector that is arranged opposite to said X-ray tube by sandwiching said subject that has been placed on said top board, the X-ray detector having a plurality of detection elements arranged in the spreading direction of said fan angle; a drive part configured to move said top board relative to said mount along the body-axis direction of said subject; a rotating part configured to support said X-ray tube and said X-ray detector to said mount to be integrally rotatable about the body axis of said subject; a rotation controlling part configured to control said rotating part so as to cause said X-ray tube to stop at a first position located above said subject or a second position located to the side of said subject; an imaging-condition setting part configured to set a plurality of CT-image imaging conditions, including an electric amount for driving and controlling the X-ray tube during CT imaging, based on a scout image that has been imaged by irradiating X-rays from said X-ray tube, to said subject on said top board that has been moved relative to a specified position by said drive part, that has been stopped at least one of said first position and said second position; and a judging part configured to judge whether any of said detection elements is expected to detect an X-ray dosage exceeding a predetermined value and to output the judgment result when capturing CT images based on the set CT-image imaging conditions.

The first aspect of the invention allows to judge presence of detection elements expected to overflow in order to output the judgment result. Usage of the judgment result allows avoiding generation of an overflow by detection elements.

A second aspect of the invention is according to the first aspect of the invention further comprising: a display part; and a display controlling part configured to cause said display part to display changes of one or more of said CT-image imaging conditions upon receiving the judgment result that any of said detection elements is expected to detect an X-ray dosage exceeding said predetermined value.

The second aspect of the invention allows to receive information about presence of detection elements expected to overflow to display a change of an imaging condition of CT images. Thus it becomes possible to allow an engineer to recognize a possibility of generation of an overflow by detection elements.

A third aspect of the invention is according to the first aspect of the invention further comprising: a determining part, based on information of the arranged positions of said detection elements that are expected to detect an X-ray dosage exceeding said predetermined value, configured to determine whether at least one of the shift amounts of said horizontal position and said vertical positions of said top board exceeds a predetermined value and outputs said determination result; and a position adjusting part configured to adjust the position of said top board in the horizontal and vertical directions that are orthogonal to the body-axis direction of said subject, wherein said position adjusting part, upon receiving a determination result provided by said determining part that said horizontal position shift of said top board exceeds a predetermined value, configured to adjust said horizontal position of said top board so as to eliminate the shift amount of said horizontal position of said top board, and, upon receiving a determination result provided by said determining part that said vertical position shift of said top board exceeds a predetermined value, is configured to adjust said vertical position of said top board so as to eliminate the shift amount of said vertical position of said top board.

The third aspect of the invention allows adjustment of the top board when the displacement of the top board exceeds a predetermined value. Thus, it is possible to avoid generation of an overflow by detection elements.

A fourth aspect of the invention is according to the first aspect of the invention further comprising: a voltage supplying part configured to supply a voltage for driving and controlling said X-ray tube; and a voltage controlling part configured to control said supplied voltage, wherein said voltage controlling part, upon receiving a determination result that any of said detection elements is expected to detect an X-ray dosage exceeding said predetermined value, is configured to control said electric amount so as to introduce an X-ray dosage below said predetermined value to said detection elements.

A fifth aspect of the invention is a recording medium that stores a control program for an X-ray CT system, the X-ray CT system comprising: a mount; an X-ray tube that irradiates a beam with a fan angle; a top board on which a subject is placed; an X-ray detector that is arranged opposite to said X-ray tube by sandwiching said subject that has been placed on said top board, the X-ray detector having a plurality of detection elements arranged in the spreading direction of said fan angle; a drive part that moves said top board relative to said mount along the body-axis direction of said subject; and a rotating part that supports said X-ray tube and said X-ray detector to said mount to be integrally rotatable about the body axis of said subject, wherein the control program causes the computer to execute: a function that causes said X-ray tube to stop at least a first position located above said subject and a second position located to the side of said subject; a function that images a scout image by irradiating X-rays from said X-ray tube, to said subject on said top board that has been moved relative to a specified position by said drive part, that has been stopped at least one of said first position and said second position; a function that determines a plurality of CT-image imaging conditions, including an electric amount for driving and controlling the X-ray tube during CT imaging, based on said imaged scout image; and a function that judges whether any of said detection elements is expected to detect an X-ray dosage exceeding a predetermined value and outputs the judgment result when capturing CT images based on the set CT-image imaging conditions.

A sixth aspect of the invention is according to the fifth aspect of the invention, the control program further comprising: a function that causes a display part to display changes of one or more of said CT-image imaging conditions upon receiving the judgment result that any of said detection elements is expected to detect an X-ray dosage exceeding said predetermined value.

A seventh aspect of the invention is according to the fifth aspect of the invention, the control program further comprising: a function that, based on information of the arranged positions of said detection elements that are expected to detect an X-ray dosage exceeding said predetermined value, determines whether at least one of the position shifts of said horizontal position and said vertical position of said top board exceeds a predetermined value and outputs said determination result; a function that adjusts the position of said top board in the horizontal and vertical directions that are orthogonal to the body-axis direction of said subject; and a function that, upon receiving a determination result that said horizontal position shift of said top board exceeds a predetermined value, adjusts said horizontal position of said top board so as to eliminate the shift amount of said horizontal position of said top board, and, upon receiving a determination result that said vertical position shift of said top board exceeds a predetermined value, adjusts said vertical position of said top board so as to eliminate the shift amount of said vertical position of said top board.

A eighth aspect of the invention is according to the fifth aspect of the invention, the control program further comprising: a function that, upon receiving a determination result that any of said detection elements is expected to detect an X-ray dosage exceeding said predetermined value, controls said electric amount so as to introduce an X-ray dosage below said predetermined value to said detection elements.

A ninth aspect of the invention is a method of determining an imaging result in case of capturing CT images by means of an X-ray CT system, the X-ray CT system comprising: a mount; an X-ray tube configured to irradiate a beam with a fan angle; a top board on which a subject is placed; an X-ray detector that is arranged opposite to said X-ray tube by sandwiching said subject that has been placed on said top board, the X-ray detector having a plurality of detection elements arranged in the spreading direction of said fan angle; a drive part configured to move said top board relative to said mount along the body-axis direction of said subject; a rotating part configured to support said X-ray tube and said X-ray detector to said mount to be integrally rotatable about the body axis of said subject; and a rotation controlling part configured to control said rotating part so as to cause said X-ray tube to stop at a first position located above said subject or a second position located to the side of said subject; the method comprising:

setting a plurality of CT-image imaging conditions, including an electric amount for driving and controlling the X-ray tube during CT imaging, based on a scout image that has been imaged by irradiating X-rays from said X-ray tube, to said subject on said top board that has been moved relative to a specified position by said drive part, that has been stopped at least one of said first position and said second position; and judging whether any of said detection elements is expected to detect an X-ray dosage exceeding a predetermined value and to output the judgment result when capturing CT images based on the set CT-image imaging conditions.

BRIEF DESCRIPTION OF THE DRAWINGS

FIGS. 5A and 5B shows a subject body on a top board set on a position displaced in a direction of height.

DETAILED DESCRIPTION OF THE EMBODIMENTS (Configuration)

Figure 1:
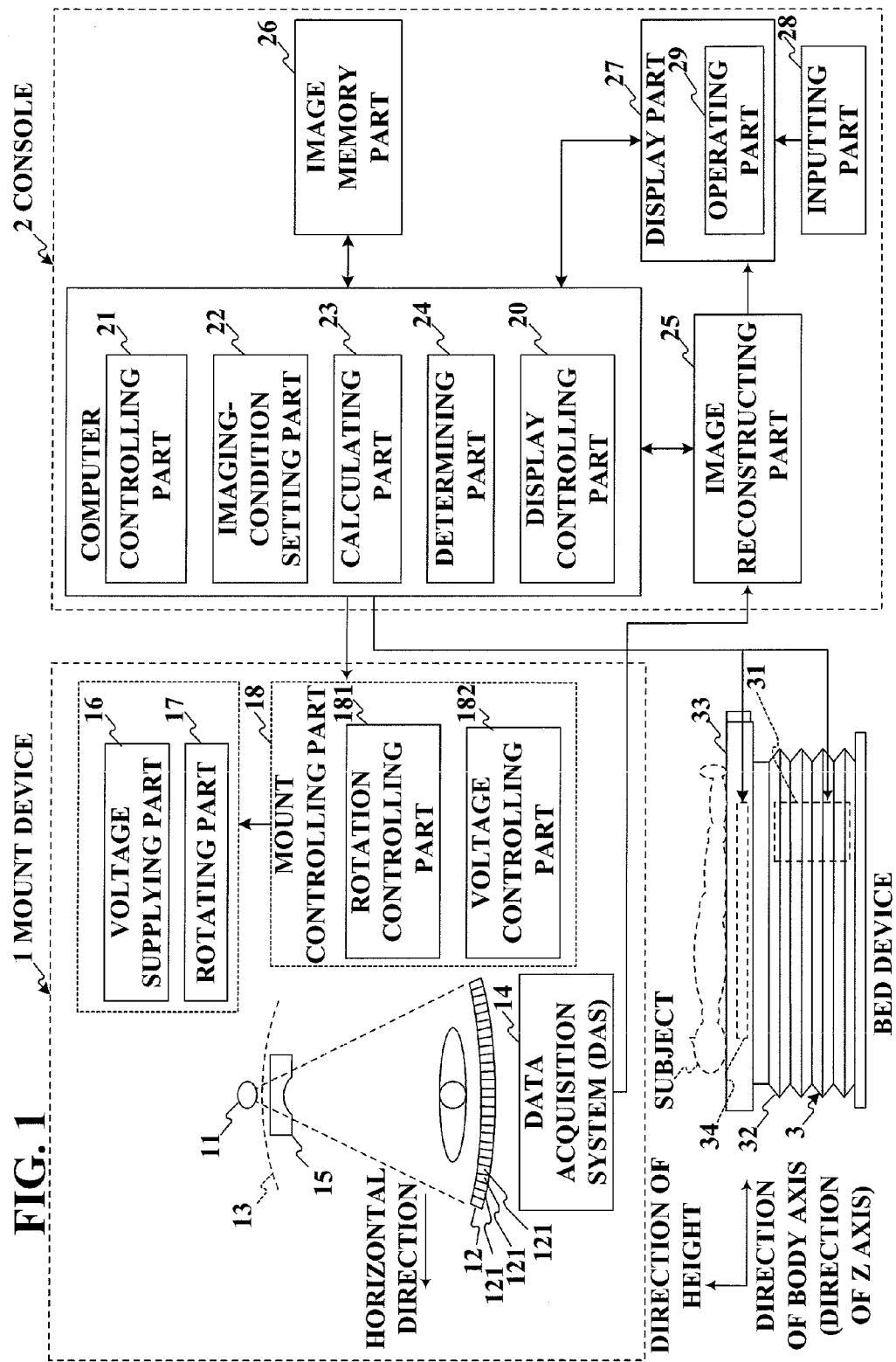
FIG. 1 is a block diagram of a structure of an X-ray CT system according to an embodiment of this invention.
Figure 2:
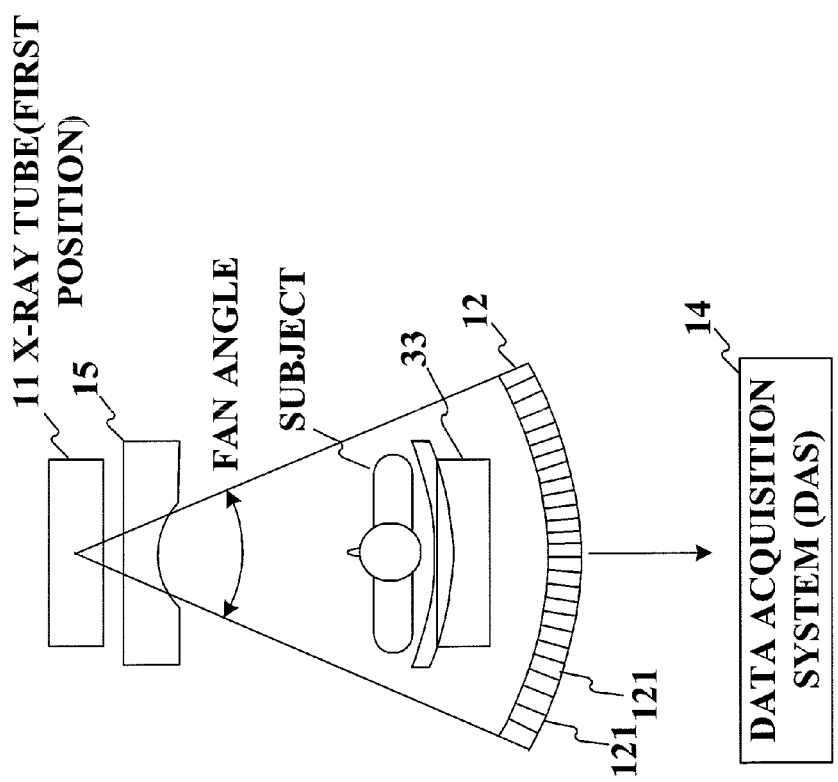
FIG. 2 shows scout image capturing by irradiating from an x-ray tube at 0 degree of a rotation position.
Figure 3:
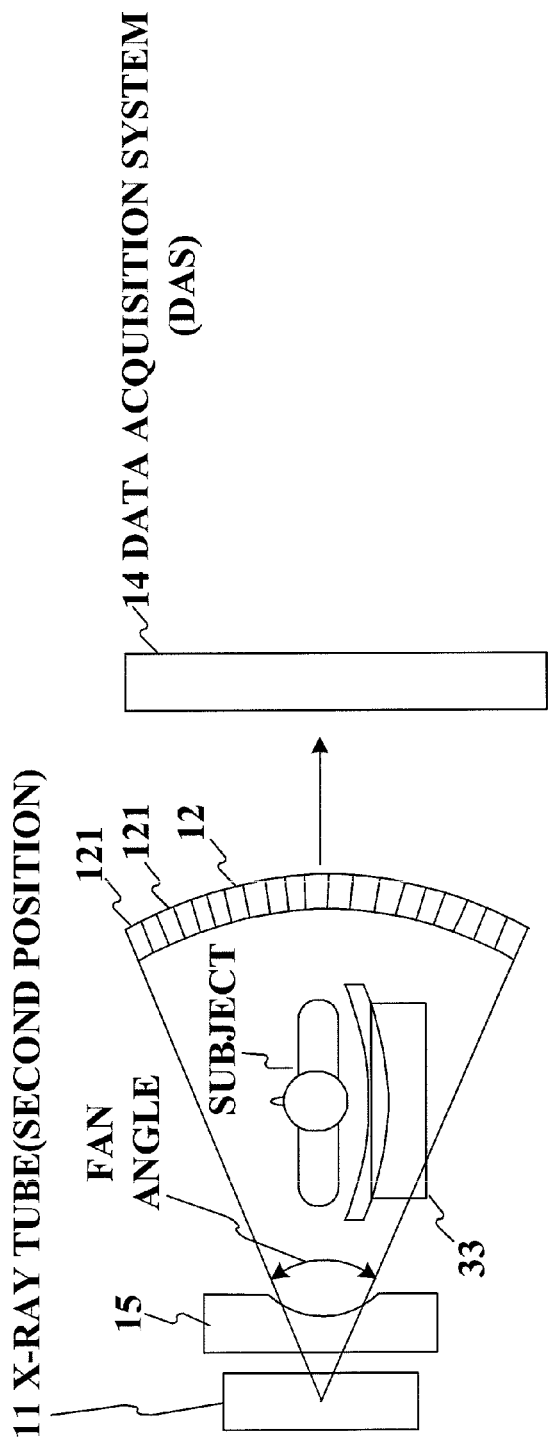
FIG. 3 shows scout image capturing by irradiating from an x-ray tube at 90 degrees of a rotation position.

An apparatus according to embodiments of the present invention will be described with reference to the figures. FIG. 1 is a block diagram showing a configuration of an X-ray CT system; FIG. 2 shows a process of scout imaging in a case of irradiating from an X-ray tube that has been stopped at the position of a rotation angle of 0°; and FIG. 3 shows a process of scout imaging in a case of irradiating from an X-ray tube that has been stopped at the position of a rotation angle of 90°.

The X-ray CT system according to this embodiment comprises a mount device 1, a console 2, and a bed device 3.

The mount device 1 comprises an X-ray tube 11 that irradiates a beam with a fan angle, an X-ray detector 12, a gantry 13, a data acquisition system (DAS) 14, a wedge filter 15 that adjusts the X-ray dosage introduced to the X-ray detector 12, a voltage supplying part 16 that supplies an electric amount for driving and controlling the X-ray tube 11, a rotating part 17 that drives the gantry 13, and a mount controlling part 18. Herein, the electric amount includes a tube voltage and tube current.

The console 2 comprises a display controlling part 20, a controlling part 21, an imaging-condition setting part 22, a calculating part 23, a determining part 24, an image reconstructing part 25, an image memory part 26, a display part 27, an inputting part 28, and an operating part 29.

The bed device 3 comprises a drive part 31, a bed base 32, a top board 33 on which the subject is placed, and a position adjusting part 34.

The X-ray detector 12 is arranged opposite to the X-ray tube 11 by sandwiching the subject that has been placed on the top board 33 and has a plurality of detection elements 121, 121, [ . . . ] that are arranged in the spreading direction of the fan angle. The gantry 13 holds the X-ray tube 11 and the X-ray detector 12 inside. The rotating part 17 causes the X-ray tube 11 and the X-ray detector 12 to rotate integrally about the body axis of the subject (about the rotation axis passing through the midpoint between the X-ray tube 11 and the X-ray detector 12) via the gantry 13. The mount controlling part 18 has a rotation controlling part 181 that controls the rotating part 17 and a voltage controlling part 182 that controls the voltage supplied from the voltage supplying part 16 to the X-ray tube 11.

The voltage supplying part 16 supplies, to the X-ray tube 11, a high voltage for exposing X-ray beams from the X-ray tube 11 according to a control signal from the voltage controlling part 182. The X-ray tube 11 exposes X-ray beams with a high voltage supplied by the voltage supplying part 16. The X-ray beams exposed by the X-ray tube 11 form either a fan beam or a cone beam. Each detection element 121 of the X-ray detector 12 detects the X-ray beams that have been exposed from the X-ray tube 11 and transmitted through the subject.

The data acquisition system 14 includes data acquisition elements that are arranged in an array form as with the detection elements 121 of the X-ray detector 12 and acquires an output value (X-ray beam signal) from each detection element 121 by matching the output value with the control signal output by the voltage controlling part 182. This acquired data is to be projection data. The projection data is associated with each code representing: a view representing the rotation angle of the X-ray tube 11 during the acquisition of the data; a channel number; a line number; the position of the top board 33. The data acquisition system 14 converts the signal outputted from the X-ray detector 12 for each channel into a voltage signal, amplifies it, and further converts it into a digital signal.

The image reconstructing part 25 reconstructs the image data by performing a back-projection process of the projection data. After storing the reconstructed image data in the image memory part 26, based on an instruction input by the operator in the inputting part 28, the image data is converted, according to a known method, into image data such as a tomogram at any cross section, a projection image from any direction, or a three-dimensional image through rendering and is output to the display part 27. The display controlling part 20 causes a monitor of the display part 27 to display the operating part 29, which is a graphical user interface (GUI). The display controlling part 20 receives the specification of the operating part 29 provided by the inputting part 28 and outputs control information, etc. to the controlling part 21.

The drive part 31 receives an instruction from the controlling part 21 and moves the top board 33 relative to the mount device 1 along the body-axis direction of the subject. Additionally, the position adjusting part 34 receives an instruction from the controlling part 21 and adjusts the position of the top board 33 on which the subject has been placed in the horizontal and vertical directions relative to the body axis of the subject (Z-axis direction).

In the X-ray CT system that is configured as described above, a scout image is imaged under the scout-image imaging conditions and CT images are thereafter imaged under the CT-image imaging conditions. Upon receiving the specification of the operating part 29 provided by the inputting part 28, the controlling part 21 issues instructions for each predetermined scout-image imaging condition to the drive part 31, the rotation controlling part 181, and the voltage supplying part 16. Each scout-image imaging condition is stored in the computer.

Upon receiving the scout-image imaging conditions, the drive part 31 moves the top board 33 relative to the mount along the body-axis direction of the subject and stops the top board 33 at the specified position. Upon receiving the scout-image imaging conditions, the rotation controlling part 181 controls the rotating part 17 and causes the X-ray tube 11 to stop at a first position (0° position) located above the subject on the top board and a second position (90° position) located to the side of the subject on the top board 33. FIG. 2 shows the X-ray tube 11 in a state in which it has been stopped at the first position. FIG. 3 shows the X-ray tube 11 in a state in which it has been stopped at the second position. Upon receiving the scout-image imaging conditions, the voltage controlling part 182 controls the voltage supplying part 16 and causes the X-ray tube 11 to irradiate X-rays to the subject.

The X-ray detecting part 12 detects said irradiated X-rays, and the data acquisition system 14 acquires a signal output from the X-ray detector 12 for each detection element (channel) 121 and converts the signal output from the X-ray detector 12 into a digital signal, and the image reconstructing part 25 reconstructs the image data, and the controlling part 21 stores the image data in the image memory part 26.

The image data is converted into the image data of the scout image based on an instruction input into the inputting part 28 by the operator and is displayed on the display part 27.

In cases in which the image data acquired by scout-image imaging is within a predetermined range, based on the scout-image imaging conditions used during the acquisition of that image data, the imaging-condition setting part 22 sets the CT-image imaging conditions by referring to a condition-matching table. The condition-matching table represents the matching relationship between the scout-image imaging conditions and the CT-image imaging conditions and is stored in an internal memory. Herein, the CT-image imaging conditions include tube voltage (kv), tube current (mA), X-ray dosage (Sv), field of view (FOV), collimator aperture, slice thickness, type of the wedge filter 15, operation of the wedge filter, positions of the top board 33, gain of the data acquisition system (DAS), and the position of the subject P.

When CT images are captured based on the set CT image imaging conditions, the determination part 24 determines whether any of detection element 121 is expected to detect an X-ray dosage exceeding said predetermined value (i.e. occurrence of overflow), and outputs the determination result. It should be noted that the determination part 24 is a determination part configured to determine occurrence of overflow.

Upon receiving a determination result, the display controlling part 20 causes a display part 27 to display the determination result indicating whether the overflow occurs or not. Further, the computer causes a speaker (not shown) to announce the determination result.

The above display or announcement allows an engineer to directly recognize whether an overflow occurs or not, so that the engineer can take various countermeasures to avoid overflows if it occurs, or can take actions for capturing images with recognition of occurrence of overflows.

Without limitation to the above example of utilizing the determination result, the determination result can be utilized as follows.

In response to the determination result indicating occurrence of overflows, the display controlling part 20 instructs the display part 27 to display the change of the CT-image imaging condition. By displaying the specific countermeasure that is the change of CT-image imaging condition, the burden of the engineer for capturing CT images is reduced. Based on the displayed specific countermeasure, the engineer changes the CT-image imaging condition by manual operation (operation through the operation part 29).

Further, since the occurrence of the overflow is expected to be caused by massive X-ray emission, the X-ray dosage is adjusted.

Further, since displacement of the top board 33 on which the subject P is placed is also expected, the displacement of the top board 33 is adjusted.

First, the adjustment of the amount of the X-ray is explained as follows.

When imaging under the CT-image imaging conditions, based on an amount of the X-ray entered into each detection element 121, an instruction is sent to the voltage controlling part 182. In response to the instruction from the controlling part 21, the voltage controlling part 182 adjusts a voltage supplied from the voltage supply part 16 to the X-ray tube 11. Thereby, the amount of X-ray entered from the X-ray tube 11 into the detection element 121 becomes below the predetermined value.

Next, an adjustment of the displacement of the top board 33 is explained as follows.

First, the shift amount of the horizontal position of the top board 33 is obtained. Under the CT-image imaging conditions (tube voltage, tube current, etc.) that have been set by the imaging-condition setting part 22, when it is assumed that the X-rays are irradiated from the X-ray tube 11 that has been stopped at the first position, the calculating part 23 estimates the X-ray dosage introduced to the detection elements 121, the calculating part 23 obtains the arranged positions of the detection elements 121 that are expected to detect an X-ray dosage exceeding a predetermined value, and the calculating parts 23 obtains the shift amount of the horizontal position of the top board 33 based on information of the arranged positions.

Additionally, when it is assumed that the X-rays are irradiated from the X-ray tube 11 when it has been stopped at the first position, it is possible to specify the position P11 of the detection element 12 in which the X-ray is most attenuated from the signal output by said each detection element (channel) 121. The calculating part 23 may obtain the shift amount of the horizontal position based on the difference (P11-P10) between the position P11 and the predetermined position P10 of the detection element 121 in which the X-ray is most attenuated. It should be noted that the predetermined position P10 of the detection element 121 is the position of the detection element 121 centrally arranged among the arranged detection elements 121.

Additionally, the shift amount of the vertical position of the top board 33 is obtained as follows. Under the CT-image imaging conditions including a tube voltage and tube current that have been set by the imaging-condition setting part 22, when it is assumed that the X-rays are irradiated from the X-ray tube 11 when it has been stopped at the second position, the calculating part 23 estimates the X-ray dosage introduced to the detection elements 121, the calculating part 23 obtains the arranged positions of the detection elements 121 that are expected to detect an X-ray dosage exceeding a predetermined value, and the calculating parts 23 obtains the shift amount of the vertical position of the top board 33 based on information of the arranged positions.

Additionally, when it is assumed that the X-rays are irradiated from the X-ray tube 11 when it has been stopped at the second position, it is possible to specify the position P21 of the detection element 121 in which the X-ray is most attenuated from the signal output by said each detection element (channel) 121. The calculating part 23 may obtain the shift amount of the horizontal position based on the difference (P21-P20) between the position P21 and the predetermined position P20 of the detection element 121 in which the X-ray is most attenuated. It should be noted that the predetermined position P20 of the detection element 121 is, as the above mentioned position P10, the position of the detection element 121 centrally arranged among the arranged detection elements 121.

Meanwhile, the calculating part 23 may obtain the shift amount of either the horizontal position or the vertical position of the top board 33.

The description about determining each displacement of the top board 33 in horizontal and vertical directions is as above.

Upon receiving the shift amounts of the horizontal position and the vertical position obtained by the calculating part 23, the determination part 24 determines whether the shift amount of the horizontal position of the top board 33 exceeds a predetermined value.

The determining part 24 also determines whether the shift amount of the vertical position of the top board 33 exceeds a predetermined value. The determining part 24 outputs a determination result to the display controlling part 20.

As described above, when capturing CT images based on the set CT-image imaging conditions, the position of the detection element 121 in which an overflow is determined to occur is detected to determine the displacement of the subject (patient) on the top board 33 to determined whether the determined displacement exceeds a predetermined value. However, the estimation of the displacement is not limited to this. For example, when it is found that the output values of the detecting elements 121 in the center are higher than expected compared to the output values of other detection elements 121 (i.e., when the introduced X-ray dosage exceeds a predetermined value) by detecting the output value (X-ray beam signal) from each detection element 121 during scout imaging, it is assumed that the shift amount of the position of the subject (patient) on the top board 33 exceeds a predetermined value.

The following description is that when the displacement amount of the top board 33 exceeds a predetermined value, the displacement amount is displayed so that an engineer adjusts the displacement of the top board 33 based on the displayed displacement amount of the top board 33, and the displacement of the top board 33 is automatically adjusted based on the displayed displacement amount of the top board 33.

The following description is that the displacement amount is displayed so that an engineer adjusts the displacement of the top board 33 based on the displacement amount of the top board 33

Upon receiving the determination result provided by the determining part 24 that the shift amount of the horizontal position of the top board 33 exceeds a predetermined value, the display controlling part 20 causes the display part 27 to display changes of one or more of the CT-image imaging conditions set by the imaging-condition setting part 22, such as changes in the tube voltage (kv), the tube current (mA), the X-ray dosage (Sv), the gain of the data acquisition system 14, or the horizontal position of the subject P. For example, upon receiving the determination result provided by the determining part 24 that the shift amount of the horizontal position of the top board 33 exceeds a predetermined value, the display controlling part 20 causes the display part 27 to display the change of the horizontal position of the top board 33. At this moment, the display controlling part 20 may cause the display part 27 to display the shift amount of the horizontal position of the top board 33 obtained by the calculating part 23.

Similarly, upon receiving the determination result provided by the determining part 24 that the shift amount of the vertical position of the top board 33 exceeds a predetermined value, the display controlling part 20 causes the display part 27 to display changes of one or more of the CT-image imaging conditions set by the imaging-condition setting part 22, such as changes in the tube voltage (kv), the tube current (mA), the X-ray dosage (Sv), the gain of the data acquisition system 14, or the vertical position of the subject P. For example, upon receiving the determination result provided by the determining part 94 that the shift amount of the vertical position of the top board 33 exceeds a predetermined value, the display controlling part 20 causes the display part 27 to display the change of the vertical position of the top board 33. At this moment, the display controlling part 20 may cause the display part 27 to display the shift amount of the vertical position of the top board 33 obtained by the calculating part 23.

As described above, the displacement amount of the top board 33 is displayed on the display part 27 when at least one of the shift amounts of the horizontal position and the vertical position of the top board 33 exceeds a predetermined value, thus enabling engineers to recognize that an overflow may be generated if CT images are imaged without adjusting the displacement of the top board 33.

The engineer manually adjusts the displacement of the top board 33 as follows. As described as follows, the shift and the shift amount in the longitudinal and horizontal directions are referred to as simply the shift and the shift amount. The operating part 29 is specified via the inputting part 28 based on the shift amount of the position of the top board 33 displayed on the display part 27. The controlling part 21 receives the specification of the operating part 29 and sends instructions to the position adjustment part 34. After receiving instructions from the controlling part 21, the position adjustment part 34 adjusts the positional displacement of the top board 33.

The following description is about an automatic adjustment of the positional displacement of the top board 33 based on the displacement amount of the top board 33.

The controlling part 21 receives the determination result provided by the determining part 24 that the shift amount of the top board 33 exceeds a predetermined value and outputs an instruction to the position adjusting part 34. The position adjusting part 34 adjusts the position of the top board 33 so as to eliminate the shift amount of the position of the top board 33. Eliminating the shift amounts of the horizontal and vertical positions of the top boards 33 enables the center of the subject to be located on the centerline that bisects the fan angle of the X-ray tube 11. It is noted that the top board 33 may be moved so that the position P10 is shifted to the position P11 in order to eliminate said position shift amount, and the top board 33 may be moved so that said detection element 121 is within the acceptable range in which no overflow is generated. Furthermore, in order to adjust the horizontal or vertical position of said top board 33, the top board 33 itself may be moved or the bed device 3 may be moved.

The above description is about an adjustment of the positional displacement of the top board 33 based on the displacement amount of the top board 33.

(Operation)

Figure 4:
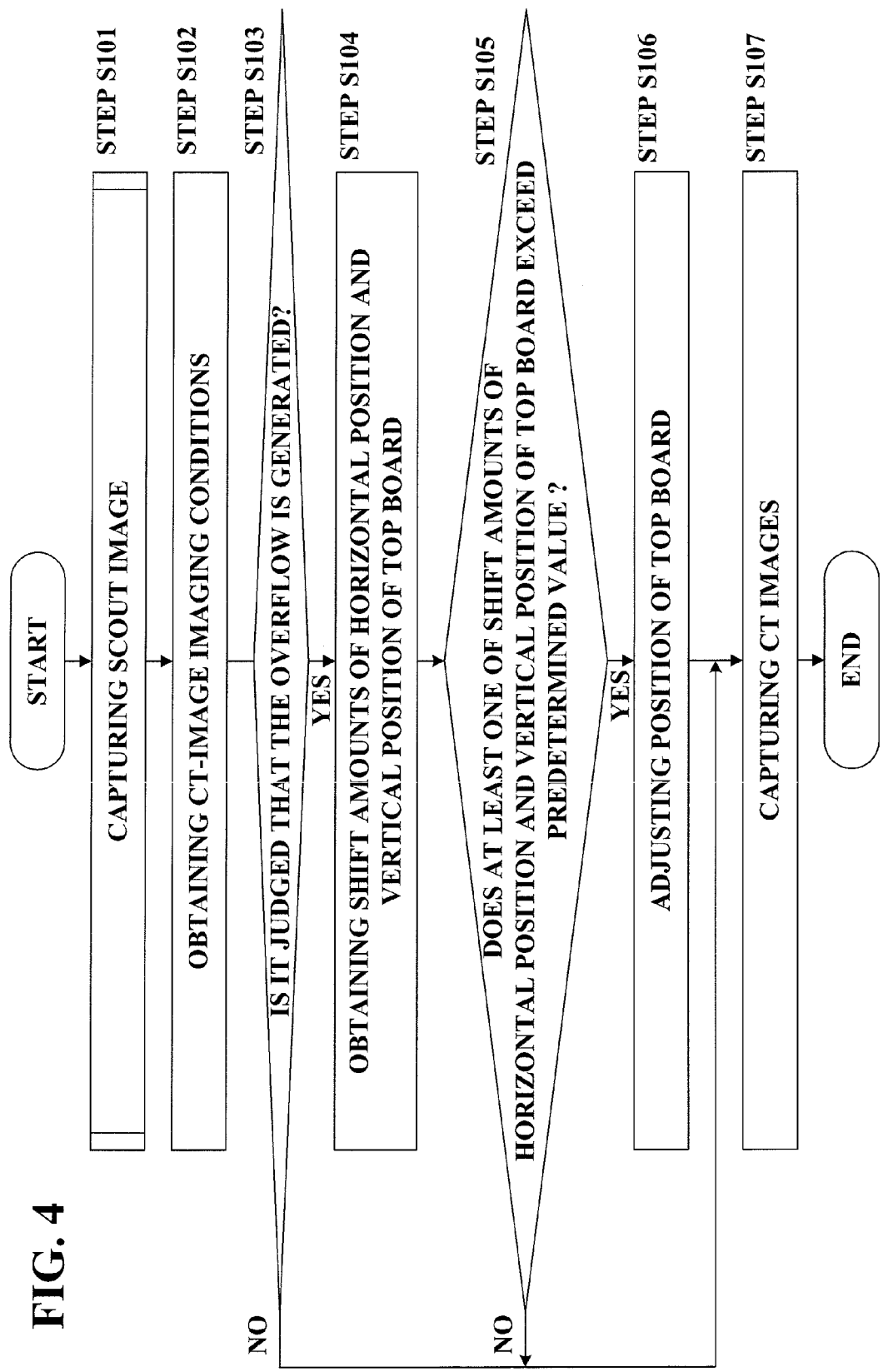
FIG. 4 is a flowchart of a series of processing for adjusting a position of a top board based on a scout image.

Now, a series of operations of firstly capturing scout images; determining occurrence of overflows in the middle; and lastly capturing CT images will be described with reference to FIG. 4, FIGS. 5A and 5B. FIG. 4 is a flow diagram showing a series of operations for adjusting the position of the top board based on a scout image, and FIGS. 5A and 5B show a subject on the top board that has been set at a position shifted in the vertical direction.

It is noted that, in the description below, X-rays are irradiated from the X-ray tube in a state in which it has been stopped at a first position located above the subject and a second position located to the side of the subject to acquire scout images related to the first position and the second position, respectively. It is also noted that the horizontal shift amount and vertical shift amount are obtained based on the scout images related to the first position and the second position.

However, the present invention is not limited to this, and the scout image related to the first position or the second position may be acquired and the horizontal shift amount or vertical shift amount of the top board 33 may be obtained based on the scout image related to the first position or the second position. Upon receiving the specification of the operating part 29 from the engineer (operator) via the inputting part 28, the controlling part 21 sets the stop position (first position and/or second position) of the X-ray tube 11.

First, the scout image is imaged (Step S101). In imaging the scout image, the drive part 31 causes the top board 33 to move to a specified position relative to the mount. The X-ray tube 11 is stopped at a first position located above the subject or a second position located to the side of the subject that has been placed on the top board 33, and the scout images are imaged by irradiating X-rays from the X-ray tube 11 that has been stopped at the first position and the second position to the subject on the top board 33 that has been moved, relative to the mount, to a specified position by the drive part 31.

Details of the scout imaging will be described below.

Based on the scout image that has been imaged in Step S101, the imaging-condition setting part 22 obtains the CT-image imaging conditions (Step S102). In this way, the CT-image imaging conditions including the tube current and tube voltage supplied to the X-ray tube 11 are obtained.

Next, when CT-images are captured based on the obtained CT-mage imaging conditions, the determination part 24 determines whether the detection element is expected to detect an X-ray dosage beyond the predetermined value (occurrence of overflow) (Step S103).

If the determination part 24 determines that overflows do not occur (Step S103; N), CT images are captured (Step S107).

If the determination part 24 determines that overflows occur (Step S103;Y), the calculating part 23 obtains the shift amounts of the horizontal position and the vertical position of the top board 33 (Step S104). In cases in which the X-rays are irradiated from the X-ray tube 11 that has been supplied with the tube current and tube voltage, etc. of the obtained CT-image imaging conditions, the calculating part 23 obtains the shift amounts of the horizontal position and the vertical position of the top board 33 based on information of the arranged positions of the detection elements 121 that are expected to detect an X-ray dosage exceeding the predetermined value.

FIG. 5A shows the shift amount δ of the vertical position of the top board 33 on which the subject is placed.

Then, when the determining part 24 determines that at least one of the shift amounts of the horizontal position or the vertical position of the top board 33 exceeds a predetermined value (Step S105;Y), the position adjusting part 34 adjusts the position of the top board 33 so as to eliminate the shift amount of the horizontal position or the vertical position that exceeds the predetermined value (Step S106). FIG. 5B shows the top board 33 in which the shift amount δ of the vertical position is eliminated, along with the subject on the top board 33.

Then, the CT images are imaged (Step S107). It is noted that when the determining part 24 determines that each of the shift amounts of the horizontal position and the vertical position of the top board 33 does not exceed a predetermined value (Step S105; N), the CT images are imaged without adjusting the position of the top board 33 (Step S107).

Figure 6:
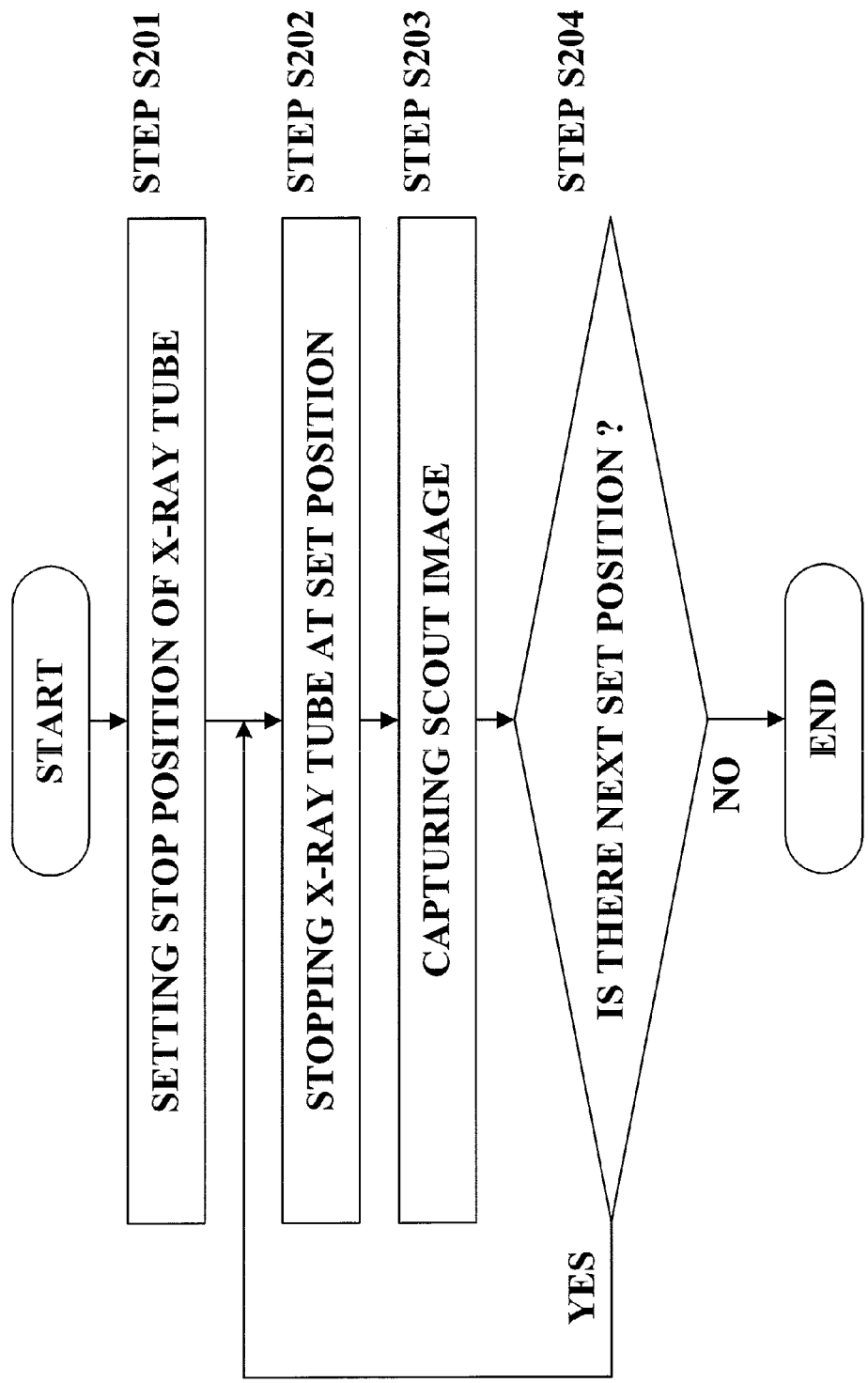
FIG. 6 is a flowchart of an imaging processing of scout images.
Figure 7:
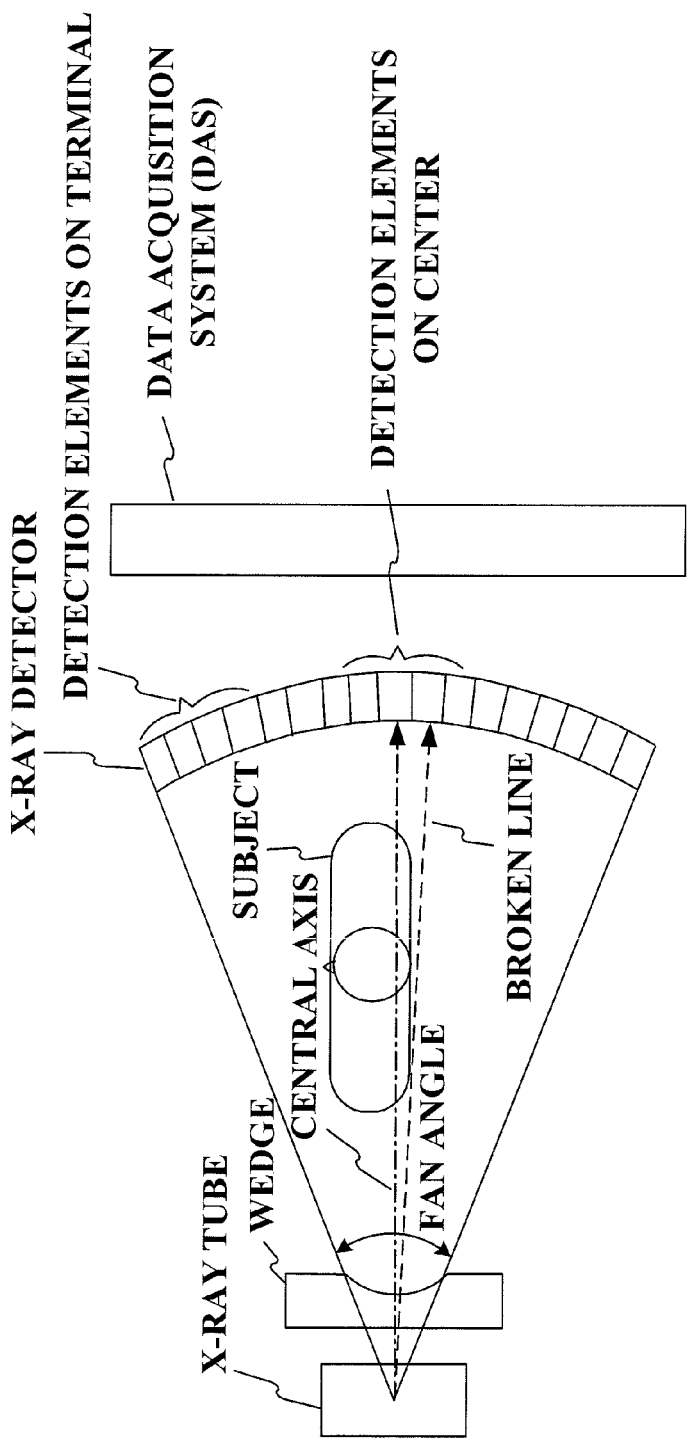
FIG. 7 shows a centerline equally dividing a fan angle and a center of a subject body on a position displaced from the centerline.

Next, the scout imaging will be described with reference to FIG. 6. FIG. 6 is a flowchart showing the operations for imaging the scout image.

First, upon receiving the specification of the operating part 29 from the engineer (operator) via the inputting part 28, the controlling part 21 sets the stop position (first position and second position) of the X-ray tube 11 (Step S201).

Then, the controlling part 21 retrieves the first set position and outputs the instruction to the rotation controlling part 181. Upon receiving the instruction from the controlling part 21, the rotation controlling part 181 causes the rotating part 17 to rotate. Thus, the X-ray tube 11 is rotated and stopped at the first position (the position located above the subject on the top board 33) that is the first set position (Step S202).

Then, under the scout-image imaging conditions, the voltage controlling part 182 controls a voltage supplied from the voltage supplying part 16 to the X-ray tube 11, causes the X-ray tube 11 to irradiate X-rays to the subject, and images the scout image (Step S203).

Then, the controlling part 21 determines whether there is a next set position (Step S204). If there is a next set position (Step S204; Y), the controlling part 21 retrieves the next set position and outputs the instruction to the rotation controlling part 181. Upon receiving the instruction from the controlling part 21, the rotation controlling part 181 causes the rotating part 17 to rotate. Thus, the X-ray tube 11 is rotated and stopped at the second position (the position located to the side of the subject on the top board 33) that is the next set position (Step S202).

Then, under the scout-image imaging conditions, the voltage controlling part 182 controls the voltage supplied from the voltage supplying part 16 to the X-ray tube 11, causes the X-ray tube 11 to irradiate X-rays to the subject, and images the scout image (Step S203).

If there is no next set position (Step S204; N) (i.e., when the scout imaging has been completed at all of the stop positions that have been set), the scout imaging is finished.

It is noted that, in the flow diagram shown in FIG. 4, the position of the top board 33 is adjusted (Step S105) and the CT images are then imaged (Step S106). However, the present invention is not limited to this, and after the position of the top board 33 is adjusted (Step S105), the operation may return to Step S101 in which the scout image is imaged, and if each of the shift amounts of the horizontal position and the vertical position of the top board 33 does not exceed a predetermined value (Step S104; N), the CT image may be imaged.

It is possible to achieve the objectives of the invention, such as the obtainment of determination information for avoiding the generation of overflow of the detection elements, by executing the processes of the control program in each step described in FIG. 4 and FIG. 6 using a computer as a hardware resource.

The above description is about automatic adjustment of the positional displacement of the top board 33 based on the positional displacement of the top board 33 if the determination part 24 determines that overflows occur (Step S103; Y). Alternatively, the voltage controlling part 182 may adjust voltages supplied from the voltage supplying part 16 to the X-ray tube 11 so that an X-ray dosage below the predetermined value is incident on the detection element 121 if the determination part 24 determines that overflows occur (Step S103; Y).

What is claimed is:

1. An X-ray CT system comprising:
   a mount;
   an X-ray tube configured to irradiate a beam with a fan angle;
   a top board on which a subject is placed;
   an X-ray detector that is arranged opposite to said X-ray tube by sandwiching said subject that has been placed on said top board, the X-ray detector having a plurality of detection elements arranged in the spreading direction of said fan angle;
   a drive part configured to move said top board relative to said mount along the body-axis direction of said subject;
   a rotating part configured to support said X-ray tube and said X-ray detector to said mount to be integrally rotatable about the body axis of said subject;
   a rotation controlling part configured to control said rotating part so as to cause said X-ray tube to stop at a first position located above said subject or a second position located to the side of said subject;
   an imaging-condition setting part configured to set a plurality of CT-image imaging conditions, including an electric amount for driving and controlling the X-ray tube during CT imaging, based on a scout image that has been imaged by irradiating X-rays from said X-ray tube, to said subject on said top board that has been moved relative to a specified position by said drive part, that has been stopped at at least one of said first position and said second position;
   a judging part configured to judge whether any of said detection elements is expected to detect an X-ray dosage exceeding a predetermined value and to output the judgment result when capturing CT images based on the set CT-image imaging conditions;
   a determining part, based on information of the arranged positions of said detection elements that are expected to detect an X-ray dosage exceeding said first predetermined value, configured to determine whether at least one of the shift amounts of said horizontal position and said vertical positions of said top board exceeds a predetermined value and outputs said determination result; and
   a position adjusting part configured to adjust the position of said top board in the horizontal and vertical directions that are orthogonal to the body-axis direction of said subject, wherein
   said position adjusting part, upon receiving a determination result provided by said determining part that said horizontal position shift of said top board exceeds a predetermined value, configured to adjust said horizontal position of said top board so as to eliminate the shift amount of said horizontal position of said top board, and, upon receiving a determination result provided by said determining part that said vertical position shift of said top board exceeds a predetermined value, is configured to adjust said vertical position of said top board so as to eliminate the shift amount of said vertical position of said top board.

2. The X-ray CT system according to claim 1, further comprising:
   a display part; and
   a display controlling part configured to cause said display part to display changes of one or more of said CT-image imaging conditions upon receiving the judgment result that any of said detection elements is expected to detect an X-ray dosage exceeding said predetermined value.

3. The X-ray CT system according to claim 1, further comprising:
   a voltage supplying part configured to supply a voltage for driving and controlling said X-ray tube; and
   a voltage controlling part configured to control said supplied voltage, wherein
   said voltage controlling part, upon receiving a determination result that any of said detection elements is expected to detect an X-ray dosage exceeding said predetermined value, is configured to control said electric amount so as to introduce an X-ray dosage below said predetermined value to said detection elements.

4. A non-transitory recording medium that stores a control program for an X-ray CT system, the X-ray CT system comprising: a mount; an X-ray tube that irradiates a beam with a fan angle; a top board on which a subject is placed; an X-ray detector that is arranged opposite to said X-ray tube by sandwiching said subject that has been placed on said top board, the X-ray detector having a plurality of detection elements arranged in the spreading direction of said fan angle; a drive part that moves said top board relative to said mount along the body-axis direction of said subject; and a rotating part that supports said X-ray tube and said X-ray detector to said mount to be integrally rotatable about the body axis of said subject, wherein the control program causes the computer to execute:
   a function that causes said X-ray tube to stop at at least a first position located above said subject and a second position located to the side of said subject;
   a function that images a scout image by irradiating X-rays from said X-ray tube-, to said subject on said top board that has been moved relative to a specified position by said drive part, that has been stopped at least one of said first position and said second position;
   a function that determines a plurality of CT-image imaging conditions, including an electric amount for driving and controlling the X-ray tube during CT imaging, based on said imaged scout image;
   a function that judges whether any of said detection elements is expected to detect an X-ray dosage exceeding a predetermined value and outputs the judgment result when capturing CT images based on the set CT-image imaging conditions;
   a function that, based on information of the arranged positions of said detection elements that are expected to detect an X-ray dosage exceeding said predetermined value, determines whether at least one of the position shifts of said horizontal position and said vertical position of said top board exceeds a predetermined value and outputs said determination result;
   a function that adjusts the position of said top board in the horizontal and vertical directions that are orthogonal to the body-axis direction of said subject; and
   a function that, upon receiving a determination result that said horizontal position shift of said top board exceeds a predetermined value, adjusts said horizontal position of said top board so as to eliminate the shift amount of said horizontal position of said top board, and, upon receiving a determination result that said vertical position shift of said top board exceeds a predetermined value, adjusts said vertical position of said top board so as to eliminate the shift amount of said vertical position of said top board.

5. The non-transitory recording medium according to claim 4, the control program further comprising:
   a function that causes a display part to display changes of one or more of said CT-image imaging conditions upon receiving the judgment result that any of said detection elements is expected to detect an X-ray dosage exceeding said predetermined value.

6. The non-transitory recording medium according to claim 4, the control program further comprising:
   a function that, upon receiving a determination result that that any of said detection elements is expected to detect an X-ray dosage exceeding said predetermined value, controls said electric amount so as to introduce an X-ray dosage below said predetermined value to said detection elements.

7. A method of determining an imaging result in case of capturing CT images by means of an X-ray CT system, the X-ray CT system comprising: a mount; an X-ray tube configured to irradiate a beam with a fan angle; a top board on which a subject is placed; an X-ray detector that is arranged opposite to said X-ray tube by sandwiching said subject that has been placed on said top board, the X-ray detector having a plurality of detection elements arranged in the spreading direction of said fan angle; a drive part configured to move said top board relative to said mount along the body-axis direction of said subject; a rotating part configured to support said X-ray tube and said X-ray detector to said mount to be integrally rotatable about the body axis of said subject; and a rotation controlling part configured to control said rotating part so as to cause said X-ray tube to stop at a first position located above said subject or a second position located to the side of said subject; the method comprising:
   setting a plurality of CT-image imaging conditions, including an electric amount for driving and controlling the X-ray tube during CT imaging, based on a scout image that has been imaged by irradiating X-rays from said X-ray tube, to said subject on said top board that has been moved relative to a specified position by said drive part, that has been stopped at at least one of said first position and said second position;
   judging whether any of said detection elements is expected to detect an X-ray dosage exceeding a predetermined value and to output the judgment result when capturing CT images based on the set CT-image imaging conditions;
   based on information of the arranged positions of said detection elements that are expected to detect an X-ray dosage exceeding said predetermined value, determining whether at least one of the shift amounts of said horizontal position and said vertical positions of said top board exceeds a predetermined value and outputs said determination result; and
   adjusting the position of said top board in the horizontal and vertical directions that are orthogonal to the body-axis direction of said subject, wherein
   said position adjusting, upon receiving a determination result provided by said determining that said horizontal position shift of said top board exceeds a predetermined value, adjusts said horizontal position of said top board so as to eliminate the shift amount of said horizontal position of said top board, and, upon receiving a determination result provided by said determining that said vertical position shift of said top board exceeds a predetermined value, adjusts said vertical position of said top board so as to eliminate the shift amount of said vertical position of said top board.

* * * * *